(12) United States Patent  
Honda et al.

(10) Patent No.: US 6,350,783 B2  
(45) Date of Patent: Feb. 26, 2002

(54) CLEANSING COMPOSITION

(75) Inventors: Shinkichi Honda, Nagareyama; Mikio Tsuboi, Komatsu, both of (JP)

(73) Assignee: Kyowa Hakko Kogyo, Tokyo (JP)

(*) Notice: Subject to any disclaimer, the term of this patent is extended or adjusted under 35 U.S.C. 154(b) by 0 days.

(21) Appl. No.: 09/185,742

(22) Filed: Nov. 4, 1998

Related U.S. Application Data

(63) Continuation of application No. 08/793,888, filed as application No. PCT/JP96/01931 on Jul. 11, 1996, now abandoned.

(30) Foreign Application Priority Data

Jul. 12, 1995 (JP) ............................................. 7-176390

(51) Int. Cl.[7] ......................... A61K 31/195; A61K 7/06; A61K 31/16; C11D 1/10
(52) U.S. Cl. ................. 514/563; 424/70.1; 424/70.19; 424/70.22; 510/126; 510/490; 510/501; 514/613; 514/975
(58) Field of Search .................. 514/975, 563, 514/613; 424/70.1, 70.19, 70.21, 70.22, 70.23, 70.24, 74, 70.27, 70.28, 70.31, 195.1; 510/126, 490, 501

(56) References Cited

U.S. PATENT DOCUMENTS

| | | | |
|---|---|---|---|
| 3,663,459 A | 5/1972 | Yoshida et al. | ............. 510/141 |
| 3,761,223 A | 9/1973 | Yoshida et al. | ................. 8/137 |
| 5,284,602 A | 2/1994 | Tachizawa et al. | .......... 510/490 |
| 5,559,092 A | 9/1996 | Gibson et al. | ................. 514/2 |
| 6,288,023 B1 * | 9/2001 | Honda et al. | ............... 510/490 |

FOREIGN PATENT DOCUMENTS

| | | |
|---|---|---|
| EP | 571198 A1 | 11/1993 |
| JP | 5438604 | 11/1979 |
| JP | 59207994 | 11/1984 |
| JP | 6027720 | 7/1985 |
| JP | 61141797 | 6/1986 |
| JP | 62124200 | 6/1987 |
| JP | 3153798 | 7/1991 |
| JP | 578693 | 3/1993 |
| JP | 583538 | 11/1993 |
| JP | 632726 | 2/1994 |
| JP | 6157284 | 6/1994 |
| JP | 6192684 | 7/1994 |
| JP | 83030 | 1/1996 |
| WO | 9014429 | 11/1990 |

* cited by examiner

*Primary Examiner*—Jose' G. Dees  
*Assistant Examiner*—Frank Choi  
(74) *Attorney, Agent, or Firm*—Antonelli, Terry, Stout & Kraus, LLP

(57) ABSTRACT

The present invention relates to a cleansing composition comprising at least one compound selected from N-long chain acylamino acids represented by formula (I):

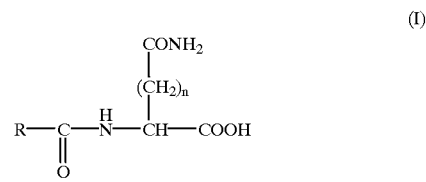

(wherein n represents 1 or 2; and R represents a saturated or unsaturated hydrocarbon group having 5 to 23 carbon atoms), and salts thereof.

10 Claims, No Drawings

CLEANSING COMPOSITION

This application is a continuation application of application Ser. No. 8,793,888, filed Mar. 12, 1997, now abandoned which is a 371 of PCT/JP96/01931, filed Jul. 11, 1996.

TECHNICAL FIELD

The present invention relates to a cleansing composition comprising an N-long chain acylamino acid or a salt thereof which composition is excellent in foaming power, foam breakage and feeling after its use.

BACKGROUND ART

Inorganic salts and organic salts of N-long chain acylamino acids have bactericidal activity in addition to surface activity. Cleansing agents comprising these salts are mild to skin and have an excellent detergency, and thus are widely used as a main component of cleansing compositions (Japanese Published Examined Patent Application No. 38604/79, Japanese Published Examined Patent Application No. 83538/93 and Japanese Published Examined Patent Application No. 27720/85).

Among the salts of N-long chain acylamino acids used as cleansing agents, salts of N-long chain acylamino acids of tertiary amide type are excellent in water-solubility, but are known to have the defects that much rinse is necessary for breaking the foam generated and that they give a slimy feeling. Salts of N-long chain acylamino acids of secondary amide type are known to be disadvantageous in that the foam is not stable enough for cleansing and that they give a poor feeling after their use. To solve these problems, it is known to use an N-long chain acyldipeptide in combination with an N-long chain acylamino acid (Japanese Published Unexamined Patent Application No. 78693/93).

N-acylglutamine is known to have hair-growing activity (Japanese Published Unexamined Patent Application No. 32726/94) and melanin formation inhibiting activity (Japanese Published Unexamined Patent Application No. 157284/94), but its use as a cleansing agent is not known.

DISCLOSURE OF THE INVENTION

The present invention provides a cleansing composition comprising at least one compound selected from N-long chain acylamino acids represented by formula (I):

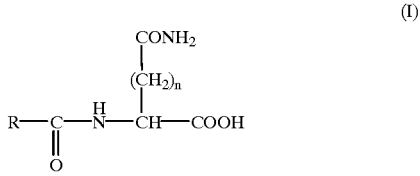

(wherein n represents 1 or 2; and R represents a saturated or unsaturated hydrocarbon group having 5 to 23 carbon atoms), and salts thereof [hereinafter referred to as Compound (I)].

Examples of the saturated hydrocarbon group having 5 to 23 carbon atoms in the definition of Compound (I) are straight-chain or branched-chain ones such as pentyl, isopentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, and tricosyl. Examples of the unsaturated hydrocarbon group having 5 to 23 carbon atoms are straight-chain or branched-chain ones such as pentenyl, 3-methyl-1-butenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, 1,3-pentadienyl, 8,11-heptadecadienyl, 8,11,14-heptadecatrienyl, and 4,7,10,13-nonadecatetraenyl.

Preferred examples of the saturated hydrocarbon group are saturated straight-chain or branched-chain hydrocarbon groups having 11 to 17 carbon atoms such as undecyl, dodecyl, tridecyl, tetradecyl, pentadecyl, hexadecyl, and heptadecyl. Preferred examples of the unsaturated hydrocarbon group are unsaturated straight-chain or branched-chain hydrocarbon groups having 11 to 17 carbon atoms such as undecenyl, dodecenyl, tridecenyl, tetradecenyl, pentadecenyl, hexadecenyl, heptadecenyl, 1,3-pentadienyl, 8,11-heptadecadienyl, and 8,11,14-heptadecatrienyl.

Examples of the salts in Compound (I) are alkali metal salts such as sodium salt, potassium salt, and lithium salt, alkaline earth metal salts such as calcium salt and magnesium salt, ammonium salt, amine addition salts such as salts with monoethanolamine, diethanolamine, triethanolamine, and triisopropanolamine, and basic amino acid addition salts such as salts with arginine and lysine.

Illustratively, the N-long chain acylamino acid consists essentially of 1–8 mol% N-octanoyl glutamine or a salt thereof, 3–10 mol% N-decanoyl glutamine or a salt thereof, 45–53 mol% N-dodecanoyl glutamine or a salt thereof, 16–25 mol% N-tetradecanoyl glutamine or a salt thereof, 5–10 mol% N-hexadecanoyl glutamine or a salt thereof, 2–10 mol% N-octadecanoyl glutamine or a salt thereof, 4–17 mol% N-octadecanoyl glutamine or a salt thereof, and 0–2 mol% N-octadecadienoyl glutamine or a salt thereof; or 1–8 mol% N-octanoyl asparagine or a salt thereof, 3–10 mol% N-decanoyl asparagine or a salt thereof, 45–33 mol% N-dodecanoyl asparagine or a salt thereof, 16–25 mol% N-tetradecanoyl asparagine or a salt thereof, 5–10 mol% N-hexadecanoyl asparagine or a salt thereof, 2–10 mol% N-octadecanoyl asparagine or a salt thereof, 4–17 mol% N-octadecanoyl asparagine or a salt thereof, and 0–2 mol% N-octadecadienoyl asparagine or a salt thereof.

Compound (I) can be prepared by converting a straight-chain or branched-chain fatty acid having 6 to 29 carbon atoms which is saturated or unsaturated (hereinafter referred to as a long chain fatty acid) into halides such as chloride and bromide by the use of halogenating agents such as thionyl chloride and phosgene, and then condensing the halide with an amino acid selected from glutamine and asparagine (hereinafter referred to simply as an amino acid). Alternatively, Compound (I) can be prepared by converting a long chain fatty acid into an acid anhydride, and then reacting the acid anhydride with an amino acid.

Examples of the long chain fatty acid are fatty acids composed of single fatty acids such as caproic acid, enanthic acid, caprylic acid, pelargonic acid, capric acid, undecylic acid, lauric acid, tridecylic acid, myristic acid, pentadecylic acid, palmitic acid, stearic acid, isostearic acid, nonadecanoic acid, arachic acid, behenic acid, lignoceric acid, oleic acid, sorbic acid, linolic acid, linolenic acid, and arachidonic acid. Fatty acids composed of these single fatty acids such as coconut oil fatty acid and palm kernel oil fatty acid can also be used.

A representative process for preparing Compound (I) via an acid halide is described below.

A long chain fatty acid is dispersed in a solvent such as methylene chloride, chloroform, carbon tetrachloride, benzene, toluene, xylene or n-hexane, and 1 to 5 equivalents of a halogenating agent is added thereto based on the long chain fatty acid to obtain a long chain fatty acid halide as a reaction product. Then, an amino acid is dissolved or dispersed in a solvent, and the above-mentioned long chain fatty acid halide is added thereto in an amount of 0.3 to 1.0 equivalent based on the amino acid, while maintaining the reaction solution at a temperature of 5 to 70° C. and thus acylation is carried out to obtain Compound (I).

Examples of the solvent used for acylation are water, methanol, ethanol, isopropanol, isobutanol, acetone, toluene, tetrahydrofuran, ethyl acetate, N,N-dimethylformamide and dimethylsulfoxide, which may be used singly or in combination. In the step where an amino acid is dissolved or dispersed in a solvent, an alkaline substance such as sodium hydroxide or potassium hydroxide in an amount of 0.8 to 2.0 equivalents based on the amino acid may also be dissolved or dispersed in the solvent as may be appropriate.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of a base to form a salt.

Compound (I) is usually employed in the cleansing composition of the present invention in an amount of 1 to 90 wt %, preferably 3 to 80 wt %.

The cleansing compositions of the present invention may be formulated to contain adjuvants such as pigments, fragrances, solubilizing agents and builders, and also surfactants such as anionic surfactants, cationic surfactants, amphoteric surfactants and nonionic surfactants to adjust foaming and detergency.

Examples of the surfactants are fatty acid soap, higher alcohol ester sulfate, polyoxyethylene higher alcohol ester sulfate, higher alcohol ester phosphate, polyoxyethylene higher fatty acid ester phosphate, salt of sulfonated higher fatty acid, salt of sulfonated higher fatty acid ester, higher fatty acid ester isethionate, salt of α-sulfo higher fatty acid ester, higher alkyldimethyl benzyl ammonium salt, higher alkylamine, higher alkyltrimethyl ammonium salt, higher fatty acid diethanolamide and its ethylene oxide or propylene oxide addition product, higher fatty acid monoethanolamide and its ethylene oxide or propylene oxide addition product, polyoxyethylene higher fatty acid monoethanol amide ester phosphate, salt of N-long chain acylamino acid such as salt of N-long chain acyl acidic amino acid, N-long chain acyl sarcosinate and salt of N-long chain acyl-β-alanine, higher alkylamino propinonate such as laurylamino propionate, higher alkylimino diacetate such as laurylimino diacetate, and amine or amide compounds such as higher alkyldimethyl betaine, higher alkyl dihydroxyethyl betaine, N-alkanoyl-N'-(2-hydroxyethyl)-N'-carboxymethylethylenediamine, and N-alkanoyl-N-(2-hydroxyethyl)-N',N'-biscarboxymethylethylenediamine.

The cleansing compositions of the present invention are useful as shampoo, facial washing compositions, bath soap, kitchen detergents, etc.

Test Examples are shown below in which the cleansing compositions of the present invention were evaluated in respect of foaming and foam breaking and also by sensory test.

Test Example 1

Sodium salt of N-lauroylglutamine obtained in Reference Example 1 and sodium salt of N-coconut oil fatty acid acylglutamine obtained in Reference Example 2 were respectively dissolved in water to prepare 30 wt % aqueous solutions (hereinafter referred to as Compositions of Invention 1 and 2, respectively). Compositions of Invention 1 and 2, and aqueous solutions respectively containing N-coconut oil fatty acid acyl-L-sodium glutamate, sodium salt of N-coconut oil fatty acid-N-methyl-β-alanine and potassium salt of N-coconut oil fatty acid acylglycin (hereinafter referred to as Comparison Compositions 1, 2 and 3, respectively) were adjusted to the concentration of 1.2 wt %. Each of the obtained aqueous solutions (100 ml) (temperature of solution: 30° C.) was poured into a graduated cylinder. Then, a stirrer bar was set therein, followed by stirring at 1500 rpm for one minute. After the end of stirring, the volume (ml) of the foam generated was measured, and also 2 minutes after the end of stirring, the volume of the foam remaining was measured.

The results are shown in Table 1.

TABLE 1

|  |  | Composition No. (Invention) | | Composition No. (Comparison) | | |
|---|---|---|---|---|---|---|
|  |  | 1 | 2 | 1 | 2 | 3 |
| Foam volume (ml) | I | 213 | 224 | 190 | 173 | 152 |
|  | II | 202 | 212 | 180 | 158 | 125 |

I: immediately after the end of stirring
II: 2 minutes after the end of stirring Test Example 2

Sensory evaluation was made on the 1.2 wt % aqueous solutions prepared in Test Example 1 by panelists consisting of 10 men and 10 women. The test solutions were used for cleansing their skin and hair, and were evaluated according to the following criteria. The average of the scores was calculated for each evaluation item and graded as follows.

| Average | ≧ 4.5 | Excellent | +++ |
|---|---|---|---|
|  | = 3.5–4.4 | Good | ++ |
|  | = 2.5–3.4 | Average | + |
|  | ≦ 2.4 | Poor | − |

A) Slimy feel in washing and E) unsmoothness feel in drying

5: very little

4: a little

3: average

2: considerable

1: very much

B) Foam breakage in rinsing

5: excellent

4: good

3: average

2: poor

1: unsatisfactory

C) Smoothness in rinsing, D) smoothness after rinsing and F) smoothness after drying 5: excellent 4: good 3: average 2: poor 1: unsatisfactory The results are shown in Table 2.

TABLE 2

| Evaluation point | Composition No. (Invention) | | Composition No. (Comparison) | | |
|---|---|---|---|---|---|
| | 1 | 2 | 1 | 2 | 3 |
| A) Slimy feeling in washing | +++ | +++ | − | + | + |
| B) Foam breakage in rinsing | +++ | +++ | ++ | ++ | + |
| C) Smoothness in rinsing | +++ | +++ | + | ++ | + |
| D) Smoothness after rinsing | ++ | ++ | − | + | − |
| E) Unsmoothness feel in drying | +++ | +++ | − | + | + |
| F) Smoothness after drying | ++ | +++ | − | + | − |

As apparent from Tables 1 and 2, the cleansing compositions of the present invention are excellent in foaming power and foam breakage and show excellent results in sensory evaluation.

Examples of the present invention are shown below.

Best Mode for Carrying Out the Invention

EXAMPLE 1

A Cleansing Cream

A cleansing cream having the following composition was prepared.

TABLE 3

| Ingredient | Composition (wt %) |
|---|---|
| (1) Sodium salt of N-coconut oil fatty acid acylglutamine (30 wt % aqueous solution) | 10.0 |
| (2) Sodium lauryl sulfate | 25.0 |
| (3) Ethylene glycol distearate | 4.0 |
| (4) Myristic acid | 8.0 |
| (5) Stearic acid | 10.0 |
| (6) Cetanol | 3.0 |
| (7) Butyl paraben | 0.1 |
| (8) Potassium hydroxide | 2.0 |
| (9) Triethanolamine | 4.0 |
| (10) Glycerin | 3.0 |
| (11) Fragrance | 0.1 |
| (12) Purified water | 30.8 |

Method for Preparation

A mixture of the ingredients (8) through (10) and (12) was heated at 80 to 90° C. to make a solution, and immediately thereafter, a solution prepared by heating a mixture of the ingredients (1) through (7) at 80 to 90° C. was added thereto gradually with stirring. Then, the ingredient (11) was added to the mixture at 60° C., followed by cooling to room temperature with stirring to obtain the product.

EXAMPLE 2

A Shampoo Liquid

TABLE 4

| Ingredient | Composition (wt %) |
|---|---|
| (1) Sodium salt of N-coconut oil fatty acid acylglutamine (30 wt % aqueous solution) | 28.0 |
| (2) Ammonium lauryl sulfate (30 wt % aqueous solution) | 20.0 |
| (3) Monoethanolamide lauryl sulfate | 2.0 |
| (4) Preservative | 0.1 |
| (5) Fragrance | 0.1 |
| (6) Purified water | 49.8 |

Method for Preparation

A mixture of the ingredients (1) through (4) and (6) was heated at 80 to 90° C., and the resulting solution was cooled gradually. Then, the ingredient (5) was added to the solution at 60° C., followed by cooling to room temperature with stirring to obtain the product.

EXAMPLE 3

Liquid Bath Soap

TABLE 5

| Ingredient | Composition (wt %) |
|---|---|
| (1) Sodium salt of N-coconut oil fatty acid acylglutamine (30 wt % aqueous solution) | 9.0 |
| (2) 2-Alkyl-N-carboxymethyl-N-hydroxyethylimidazolinium betaine (40 wt % aqueous solution) | 25.0 |
| (3) Coconut oil fatty acid diethanolamide | 5.0 |
| (4) Polyoxyethylene alkyl ether sodium sulfate (25 wt aqueous solution) | 10.0 |
| (5) Propylene glycol | 6.0 |
| (6) Sodium chloride | 1.0 |
| (7) Preservative | 0.1 |
| (8) Phosphoric acid | 0.1 |
| (9) Fragrance | 0.1 |
| (10) Purified water | 43.7 |

Method for Preparation

A mixture of the ingredients (1) through (8) and (10) was heated at 80 to 90° C., and the resulting solution was cooled gradually. Then, the ingredient (9) was added to the solution at 60° C., followed by cooling to room temperature with stirring to obtain the product.

Reference Example 1

Process for Producing N-lauroyl-glutamine (1) Halogenation Reaction

In 300 ml of methylene chloride was dispersed 100 g of lauric acid, and 35.5 g of thionyl chloride was added thereto with stirring over 30 minutes, followed by further stirring for 3 hours. The temperature of the solution was maintained at 20° C. during this reaction. After the reaction was completed, the infrared absorption spectrum of the reaction mixture was measured. It was confirmed that lauroyl chloride was formed by the fact that the peak at 1695 cm$^{-1}$ derived from carboxylic acid (—COOH) was not observed, whereas the peak at 1785 cm$^{-1}$ derived from an acid chloride (—COCl) was observed. After methylene chloride, thionyl chloride and hydrogen chloride were distilled off under reduced pressure, with nitrogen gas being passed through the reaction mixture, the fraction distilled at 150° C. under reduced pressure (22 mHg) was recovered to give 96 g of lauroyl chloride.

(2) Acylation Reaction

In a solution of 19.5 g of potassium hydroxide in 75 ml of water was dispersed 50 g of glutamine. To the obtained solution were added dropwise with stirring a solution of 72 g of lauroyl chloride obtained in (1) in 145 ml of tetrahydrofuran and 73.9 g of a 25% aqueous solution of potassium hydroxide over one hour, during which the solution was kept at 20° C. The resulting mixture was stirred at the same temperature for 4 hours. Then, 6 N hydrochloric acid was added to the mixture with stirring until the pH of the mixture reached 1.0, followed by further stirring for one hour. After the reaction was completed, the precipitated crystals were collected by filtration and dried to give 101.4 g of crystals. The measurement of the infrared absorption spectrum and the elementary analysis were carried out on the obtained crystals.

Infrared absorption spectrum (KBr tablet) (cm$^{-1}$): 1735, 1650, 1565

Elementary analysis ($\delta$): $C_{12}H_{32}O_4N_2$ Calcd: C,62.17; H,9.82; N,8.53. Found: C,62.42; H,9.69; N,8.43.

The above results confirmed that the crystals were N-lauroyl glutamine.

Reference Example 2

Process for Producing N-coconut oil Fatty Acid Acylglutamine (1) Halogenation Reaction In 300 ml of methylene chloride was dispersed 100 g of coconut oil fatty acid, and 30.2 g of thionyl chloride was added thereto with stirring over 30 minutes, followed by further stirring for 3 hours. The temperature of the solution was maintained at 20° C. during this reaction. After the reaction was completed, the infrared absorption spectrum of the reaction mixture was measured. It was confirmed that lauroyl chloride was formed by the fact that the peak at 1695 cm$^{-1}$ derived from carboxylic acid (—COOH) was not observed, whereas the peak at 1785 cm$^{-1}$ derived from an acid chloride (—COCl) was observed. After methylene chloride and thionyl chloride, as well as sulfur dioxide and hydrogen chloride formed as by-products, were distilled off under reduced pressure, the fraction distilled at 105 to 200° C. under reduced pressure (5 mmHg) was recovered to give 92.8 g of coconut oil fatty acid chloride.

(2) Acylation Reaction

In a solution of 19.5 g of potassium hydroxide in 75 ml of water was dispersed 50 g of glutamine. To the obtained solution were added dropwise with stirring a solution of 82.2 g of coconut oil fatty acid chloride obtained in (1) in 145 ml of tetrahydrofuran and 73 g of a 25% aqueous solution potassium hydroxide, during which the solution was kept at 35 to 40° C. and at pH 8.5 to 9.5 over one hour. The resulting mixture was stirred at the same temperature for 4 hours. Then, 6 N hydrochloric acid was added to the mixture with stirring until the pH of the mixture reached 1.0, followed by further stirring for one hour. After the reaction was completed, the precipitated crystals were collected by filtration and dried to give 104.9 g of crystals. The measurement of the infrared absorption spectrum and the elementary analysis were carried out on the obtained crystals.

Infrared absorption spectrum (KBr tablet) (cm$^{-1}$) 1740, 1640, 1550

Elementary Analysis

Coconut oil fatty acid chloride obtained in (1) was decomposed with water, and analyzed by gas chromatography for constituent fatty acids of the coconut oil fatty acid. The average molecular weight calculated based on the fatty acid composition was 234.58. The elementary analysis values calculated based on the average molecular weight of N-coconut oil fatty acid acylglutamine and those found on the compound obtained in (2) are shown below.

Calcd: C,63.91; H,10.73; N,7.72.

Found: C,64.02; H,10.70; N,7.59.

The above results confirmed that the obtained compound was N-coconut oil fatty acid acylglutamine represented by formula (II):

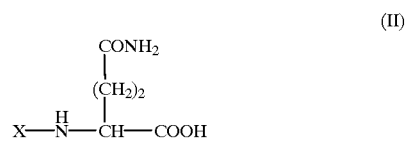

(wherein X represents an acyl group derived from coconut oil fatty acid).

Industrial Applicability

The present invention provides a cleansing composition which is excellent in foaming power, foam breakage and feeling after its use. The composition is useful as a shampoo, a facial washing composition, bath soap, and a kitchen detergent, etc.

What is claimed is:

1. A cleansing composition comprising N-coconut oil fatty acid acylglutamine or a salt thereof, and (2) a cosmetically acceptable carrier.

2. The cleansing composition according to claim 1, wherein said N-coconut oil fatty acid acylglutamine or salt thereof is produced by reacting coconut oil fatty acid with glutamine or a salt thereof.

3. The cleansing composition according to claim 1, wherein, said N-coconut oil fatty acid acylglutamine or salt thereof is an active cleaning agent in said cleansing composition.

4. The cleansing composition according to claim 1, containing a further compound which is an additional surfactant.

5. The cleansing composition according to claim 4, wherein said N-coconut oil fatty acid acylglutamine or salt thereof is contained in the composition in an amount of 1 to 90 wt %.

6. The cleansing composition according to claim 1, wherein said N-coconut oil fatty acid acylglutamine or a salt thereof is contained in the composition in an amount of 1 to 90 wt %.

7. The cleansing composition according to claim 1, wherein said N-coconut oil fatty acid acylglutamine or a salt thereof is contained in the composition in an amount of 3 to 80 wt %.

8. The cleansing composition according to claim 1, wherein the cosmetically acceptable carrier is a carrier for a shampoo, the cleansing composition being a shampoo.

9. The cleansing composition according to claim 1, wherein the cosmetically acceptable carrier is a carrier for a soap, the cleansing composition being a soap.

10. The cleansing composition according to claim 1, wherein the cosmetically acceptable carrier is a carrier for a kitchen detergent, the cleansing composition being a kitchen detergent.

* * * * *